(12) United States Patent
Ueda

(10) Patent No.: US 10,888,764 B2
(45) Date of Patent: Jan. 12, 2021

(54) METHOD FOR IDENTIFYING STATE OF ATHLETE AND DEVICE FOR IDENTIFYING STATE OF ATHLETE

(71) Applicant: PANASONIC INTELLECTUAL PROPERTY MANAGEMENT CO., LTD., Osaka (JP)

(72) Inventor: Junko Ueda, Kanagawa (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 90 days.

(21) Appl. No.: 16/301,617

(22) PCT Filed: Feb. 17, 2017

(86) PCT No.: PCT/JP2017/005874
§ 371 (c)(1),
(2) Date: Nov. 14, 2018

(87) PCT Pub. No.: WO2017/199497
PCT Pub. Date: Nov. 23, 2017

(65) Prior Publication Data
US 2019/0290990 A1    Sep. 26, 2019

(30) Foreign Application Priority Data
May 18, 2016 (JP) ................................. 2016-099367

(51) Int. Cl.
*G06K 9/00* (2006.01)
*A63B 71/06* (2006.01)
(Continued)

(52) U.S. Cl.
CPC .......... *A63B 71/06* (2013.01); *G06K 9/00342* (2013.01); *G06T 7/20* (2013.01);
(Continued)

(58) Field of Classification Search
None
See application file for complete search history.

(56) References Cited

U.S. PATENT DOCUMENTS 8,317,659 B2 * 11/2012 Woodson ........... A63B 24/0062
482/11
9,539,469 B2 * 1/2017 Lee ........................ A63B 31/00
(Continued)

FOREIGN PATENT DOCUMENTS

| JP | 2003-117041 | 4/2003 |
| JP | 2004-046647 | 2/2004 |

OTHER PUBLICATIONS

Le Sage et al., "A multi-sensor system for monitoring the performance of elite swimmers", ICETE 2010, CCIS 222, pp. 350-362, 2012 (Year: 2012).*

(Continued)

*Primary Examiner* — Soo Jin Park
(74) *Attorney, Agent, or Firm* — Greenblum & Bernstein, P.L.C.

(57) ABSTRACT

To precisely identify a state of an athlete who is present in a swimming pool, a processor used in a device for identifying a state of an athlete or a method for identifying a state of an athlete refers to a result of performing processing of detecting the athlete in a video image obtained by imaging the athlete who is present in the swimming pool and identifies an advancing direction of the athlete as a direction that is different from the previous advancing direction on the basis of a result of the detection of the athlete after the athlete is present in a region on the side of an end of the swimming pool. In this manner, it is possible to more accurately identify the advancing direction of the athlete and to thereby precisely identify the state of the athlete who is present in the swimming pool.

14 Claims, 11 Drawing Sheets

(51) Int. Cl.
*G06T 7/20* (2017.01)
*H04N 7/18* (2006.01)

(52) U.S. Cl.
CPC ............ *H04N 7/18* (2013.01); *A61B 2503/10* (2013.01); *A63B 2208/03* (2013.01); *G06T 2207/30221* (2013.01)

(56) References Cited

U.S. PATENT DOCUMENTS

2004/0201675 A1    10/2004   Murakoshi et al.
2013/0321397 A1*   12/2013   Chen ..................... G06T 17/05
                                                                345/419

OTHER PUBLICATIONS

Sha et al., "Swimmer localization from a moving camera", 2013 IEEE (Year: 2013).*
The Extended European Search Report from the European Patent Office (EPO) dated Apr. 26, 2019 for the related European Patent Application No. 17798935.7.
Long Sha et al: "Swimmer Localization from a Moving Camera", 2013 International Conference on Digital Image Computing: Techniques and Applications (DICTA), Nov. 2013 (Nov. 2013), pp. 1-8, XP055549714.
International Search Report (ISR) from International Searching Authority (Japan Patent Office) in International Pat. Appl. No. PCT/JP2017/005874, dated May 9, 2017.

* cited by examiner

METHOD FOR IDENTIFYING STATE OF ATHLETE AND DEVICE FOR IDENTIFYING STATE OF ATHLETE

TECHNICAL FIELD

The present disclosure relates to a method for identifying a state of an athlete and a device for identifying a state of an athlete.

BACKGROUND ART

In the related art, a mobile body tracking device that tracks a mobile body in a video image is known. According to a technology described in Patent Literature 1, for example, a predicted position of a mobile body in a frame image obtained this time is obtained on the basis of positional information of the mobile body in a frame image obtained in the past. Then, candidate objects that have a predetermined feature specific to the mobile body are extracted from image data of the frame image obtained this time, and a candidate object that is located at the closest position to the predicted position from among the extracted candidate objects is assigned as the mobile body.

CITATION LIST

Patent Literature

PTL 1: Japanese Patent Unexamined Publication No. 2004-46647

SUMMARY OF THE INVENTION

The present disclosure relates to a method and a device for precisely identifying a state of an athlete who is present in a swimming pool.

A method for identifying a state of an athlete and a device for identifying a state of an athlete according to the present disclosure refer to a result of performing processing of detecting an athlete in a video image and identify an advancing direction of the athlete as a direction that is different from the previous advancing direction, on the basis of a result of the detection of the athlete after the athlete is present in a region on a side of an end of the swimming pool.

The method for identifying a state of an athlete and the device for identifying a state of an athlete according to the present disclosure are advantageous for precisely specifying a state of an athlete who is present in a swimming pool.

DESCRIPTION OF EMBODIMENTS

Hereinafter, embodiments will be described in detail with reference to drawings as needed. However, there will also be cases in which unnecessarily detailed description is omitted. For example, there will be cases in which detailed description of matters that have already been well-known or overlapping description for substantially the same configurations are omitted. This is for avoiding the following description from being unnecessarily redundant and for facilitating understanding of those skilled in the art.

Note that the present inventor will provide the accompanying drawings and the following description for sufficient understanding of the present disclosure by those skilled in the art, and these are not intended to limit the subject matter described in the claims.

First Exemplary Embodiment

Hereinafter, a first exemplary embodiment will be described with reference to FIGS. 1 to 12.

[1-1. Configurations]

Figure 1:
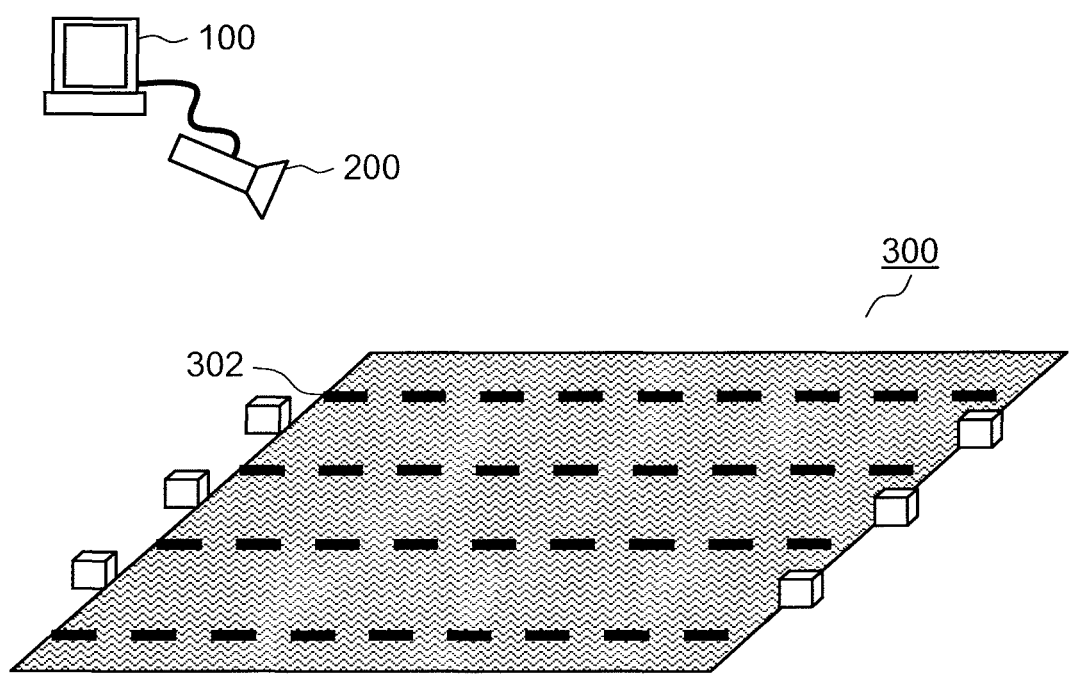
FIG. 1 is a diagram illustrating how a device for identifying a state of an athlete according to a first exemplary embodiment is used.

FIG. 1 is a diagram illustrating how a device for identifying a state of an athlete is used according to the first exemplary embodiment.

Device for identifying a state of an athlete 100 is realized by installing a program for identifying a state of an athlete on a general-purpose computer. Device for identifying a state of an athlete 100 is connected to imaging device 200 in such a manner in which it is possible to communicate with imaging device 200. Device for identifying a state of an athlete 100 may be a dedicated built-in device or may be configured as hardware. Device for identifying a state of an athlete 100 is typically a device for generating final video image content by editing a video image. Therefore, it is assumed that a user of device for identifying a state of an athlete 100 is an operator who is in charge of editing tasks for the video image.

Imaging device 200 is a video camera. Imaging device 200 images swimming pool 300 in a bird's eye view as illustrated in FIG. 1. The moving image or an image that imaging device 200 has captured is transmitted to device for identifying a state of an athlete 100.

Swimming pool 300 has a plurality of lanes. A plurality of lane marks 302 are stretched across swimming pool 300. Note that although a reference numeral is given only to a lane mark at the top in FIG. 1, the broken lines in FIG. 1 represent the lane marks. Lane marks 302 are marks for sectioning lanes. The lanes are regions between adjacent lane marks 302.

Figure 2:
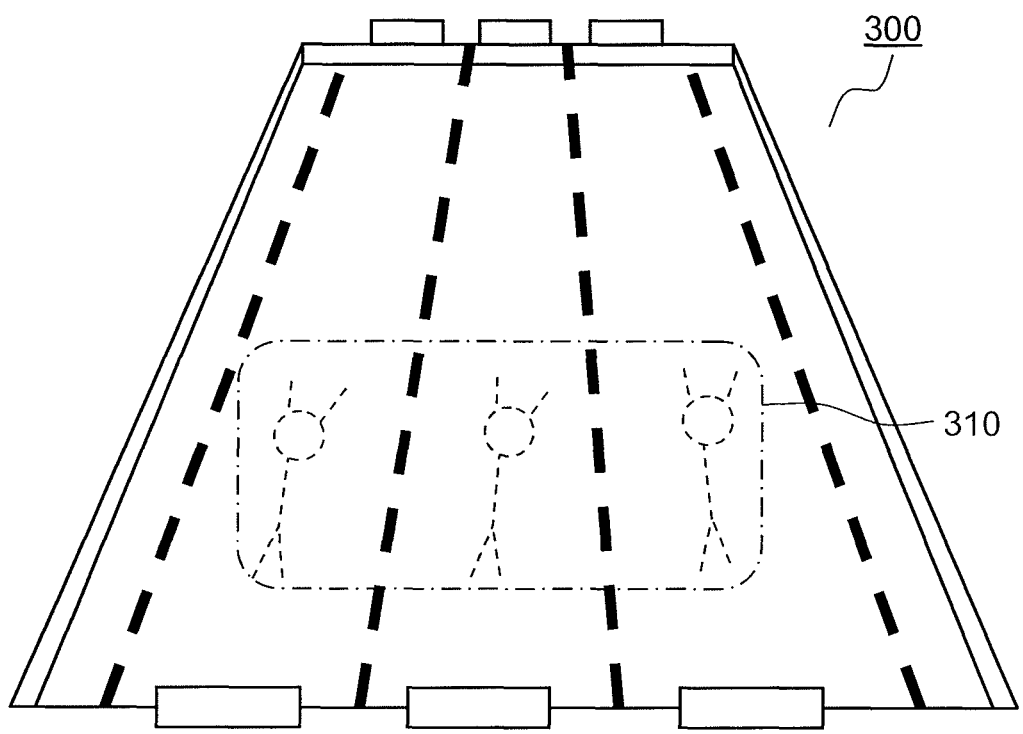
FIG. 2 is a diagram illustrating an example of a video image obtained by capturing a swimming competition image in a swimming pool according to the first exemplary embodiment.

FIG. 2 is a diagram illustrating an example of a video image obtained by capturing a swimming competition image in the swimming pool according to the first exemplary embodiment. As illustrated in FIG. 1, imaging device 200 images swimming pool 300 in a bird's eye view according to the first exemplary embodiment. Therefore, the image captured by imaging device 200 is an image in which swimming pool 300 appears to be widened from the further side to the closer side as illustrated in FIG. 2. According to the embodiment, the video image to be processed is a video image obtained by imaging swimming competition in a swimming pool. Athlete 310 is swimming in the swimming pool.

Figure 3:
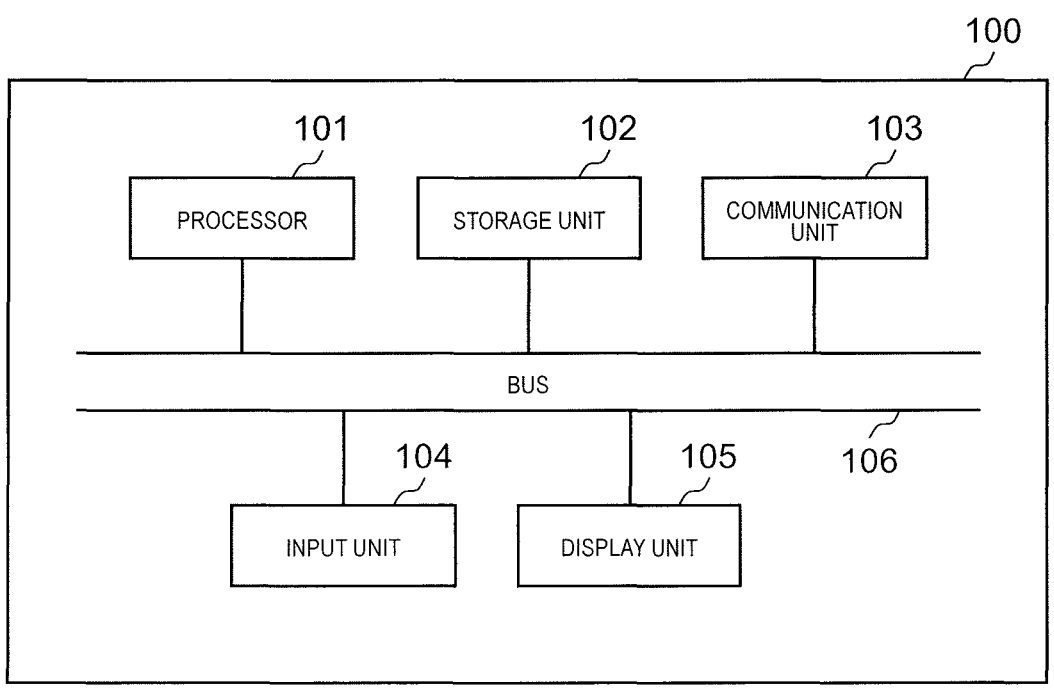
FIG. 3 is a diagram illustrating a configuration of the device for identifying a state of an athlete according to the first exemplary embodiment.

FIG. 3 is a diagram illustrating a configuration of a device for identifying a state of an athlete according to the first exemplary embodiment. Device for identifying a state of an athlete 100 has processor 101, storage unit 102, communication unit 103, input unit 104, display unit 105, and bus 106.

Processor 101 controls the other components in the device for identifying a state of an athlete by performing arithmetic operations.

Storage unit 102 temporarily or permanently stores information. Storage unit 102 corresponds to a read only memory (ROM), a random access memory (RAM), or the like in the device for identifying a state of an athlete. Device for identifying a state of an athlete 100 may be provided with a plurality of storage units 102 in accordance with a purpose of use or necessity of an access speed. It is also possible to configure storage units 102 by applying a hard disc drive (HDD), a synchronous dynamic random access memory (SDRAM), a solid state drive (SSD), or the like.

Communication unit 103 is an interface that connects device for identifying a state of an athlete 100 to imaging device 200. Communication unit 103 may be a wired connection interface or a wireless connection interface. Communication unit 103 is for transmitting a moving image or an image captured by imaging device 200 to device for identifying a state of an athlete 100. Therefore, communication unit 103 is not an essential configuration in a case in which the moving image or the image is moved from imaging device 200 to device for identifying a state of an athlete 100 by using a storage medium.

Input unit 104 receives signals from the outside. Input unit 104 corresponds to an input device, an input interface, or the like of device for identifying a state of an athlete 100. It is possible to configure input unit 104 by applying an input device such as a mouse or a keyboard or an input interface such as a communication port or a wireless communication device.

Display unit 105 displays information for the outside. It is possible to configure display unit 105 by applying a liquid crystal display or the like.

Bus 106 is a route for connecting the respective elements that configure device for identifying a state of an athlete 100. It is possible to configure bus 106 inside processor 101 by integrating bus 106 with processor 101. Bus 106 may connect the respective elements in a wired manner or may connect the respective elements in a wireless manner.

The configuration of the device for identifying a state of an athlete 100 described above is an example. Therefore, device for identifying a state of an athlete 100 may be configured by adding other components to the configuration described above. In addition, device for identifying a state of an athlete 100 may be configured by deleting a part of the components from the configuration described above as needed. In addition, device for identifying a state of an athlete 100 may be configured by mutually integrating the components described above. In addition, device for identifying a state of an athlete 100 may be configured by separating the components described above into the components described above.

[1-2. Operations]

Operations of device for identifying a state of an athlete 100 described above will be described. Note that device for identifying a state of an athlete 100 operates mainly by the processor 101 executing a program in cooperation with the respective elements in device for identifying a state of an athlete 100.

[1-2-1. Basic Operations]

Figure 4:
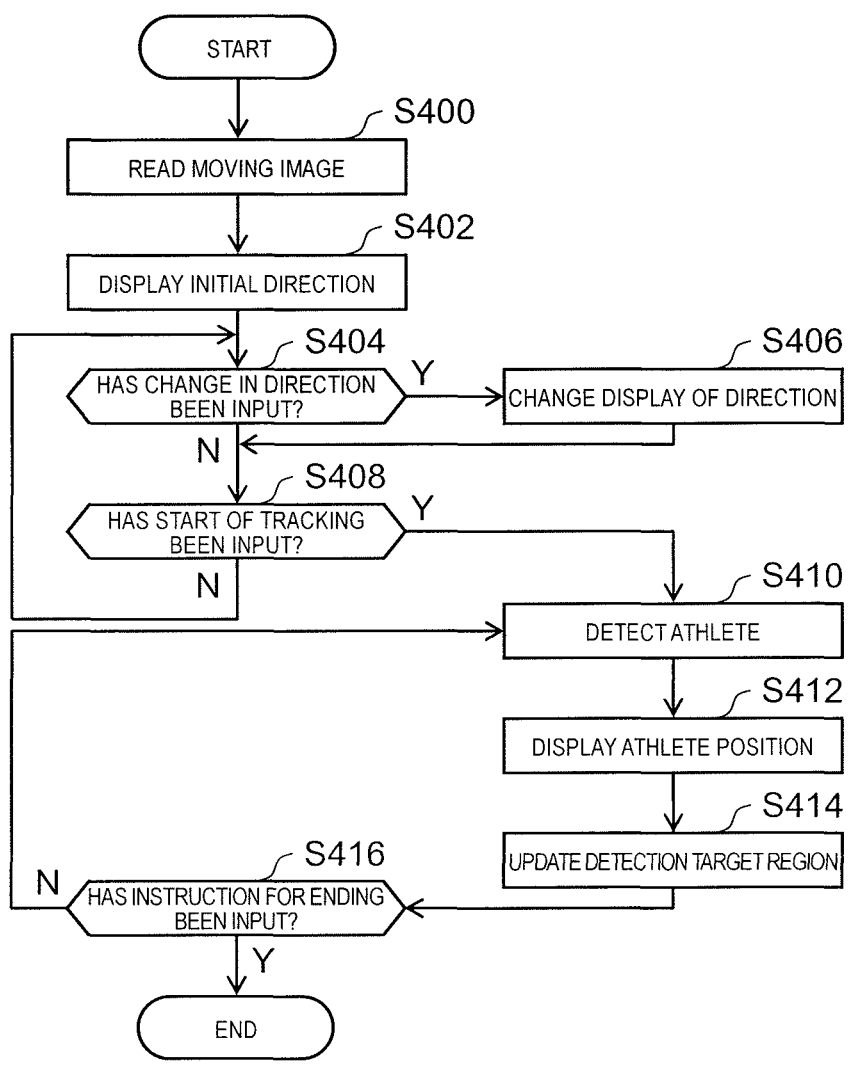
FIG. 4 is a flowchart for describing basic operations of the device for identifying a state of an athlete according to the first exemplary embodiment.

FIG. 4 is a flowchart for describing basic operations of the device for identifying a state of an athlete according to the first exemplary embodiment.

In Step S400, device for identifying a state of an athlete 100 receives a video image from imaging device 200 via communication unit 103.

Processor 101 defines where a region in which a lane appears is in a region in the moving image received in Step S400. Various methods for defining the region in which the lane appears by device for identifying a state of an athlete 100 are considered. For example, the user of device for identifying a state of an athlete 100 may designate a predetermined region in the video image via input unit 104, and processor 101 may define the designated range as the lane. Alternatively, lane marks 302 may be detected in the video image, and processor 101 may define a region between detected lane marks 302 as a lane. A plurality of lanes may be defined, or only one lane may be defined. The following processing is independently performed for each lane (and an athlete in the lane) unless otherwise particularly stated.

Processor 101 completes the definition of the lane region, then reproduces the video image, and displays the video image on display unit 105. The following processing may be performed in a state in which the video image is being reproduced or in a state in which the video image is stopped. Processor 101 recognizes an input received in the following processing as an input to one frame (image) of the video image that is being reproduced by display unit 105.

In Step S402, processor 101 displays an advancing direction of the athlete in a state in which the advancing direction is overlaid on each lane region in the video image, via display unit 105. The advancing direction displayed in Step S402 will be referred to as an initial direction.

Figure 5:
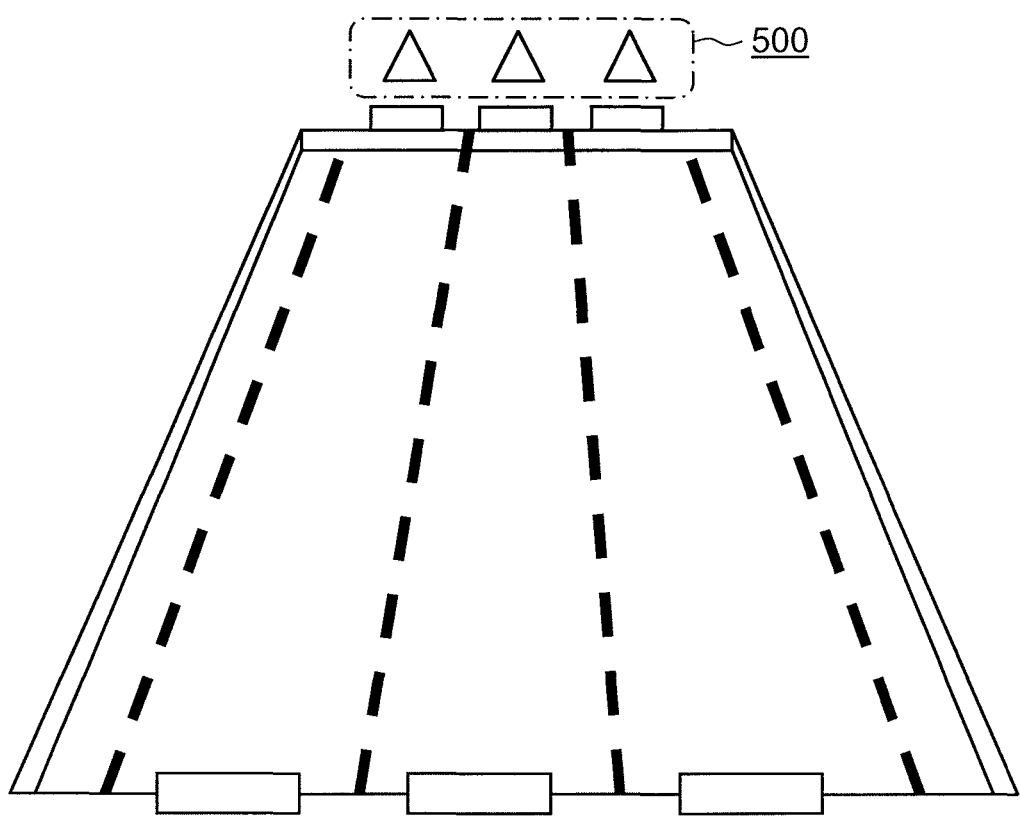
FIG. 5 is a diagram illustrating an example in which an advancing direction has been overlaid on the video image according to the first exemplary embodiment.

FIG. 5 is a diagram illustrating an example in which the advancing direction is overlaid on the video image according to the first exemplary embodiment. Advancing directions 500 are expressed as triangles directed upward in FIG. 5. Three advancing directions 500 are overlaid on the video image in such a manner that advancing directions 500 correspond to three lanes running in the longitudinal direction at the center of FIG. 5. The direction indicated by advancing directions 500 is the upward direction. In the embodiment, it is assumed that the direction in which the athlete starts to swim immediately after the start is the direction from the closer side to the further side. Therefore, the initial direction is the upward direction.

In Step S404, processor 101 determines whether or not an instruction for changing the advancing direction has been received from the user of device for identifying a state of an athlete 100. The direction in which the athlete starts to swim immediately after the start may be from the further side to the closer side in some cases depending on types of swimming competition. In such cases, the user inputs the instruction that the advancing direction is to be changed, via input unit 104.

In Step S406 (Yes in Step S404), processor 101 changes the advancing direction on the basis of the instruction for the changing, which has been received from the user of device for identifying a state of an athlete 100. Advancing directions of an athlete in swimming competition are basically two directions (a forward direction and a backward direction). Therefore, processor 101 inverts an advancing direction in response to the reception of the instruction for the changing in the embodiment. If processor 101 causes the advancing direction to be determined, the determination is reflected to display unit 105. Note that since the instruction for the changing made in Step S404 is an instruction for the changing with respect to the initial direction, the instruction is considered to be an instruction for changing the advancing direction for all the lanes rather than an instruction for changing the advancing direction in the individual lanes. Therefore, the input for changing the direction in Step S404 is performed through a simple input, such as pressing of a shortcut key of input unit 104, as an input for the changing targeted to all the lanes.

In Step S408, processor 101 determines whether or not an instruction for starting tracking has been received from the user of device for identifying a state of an athlete 100. The user of device for identifying a state of an athlete 100 uses input unit 104 to input the instruction for tracking at a predetermined timing while viewing the video image that is being reproduced. In the embodiment, the predetermined timing is assumed to be a timing at which the swimming competition is started. If the instruction for tracking is input, processing of detecting the athlete from the video image is started as will be described later. If the athlete is detected before the timing at which the swimming competition is started, a load on processor 101 increases, data obtained in the processing of detecting the athlete includes data of other than the competition, and there is thus a concern that effectiveness of the data deteriorates. Note that in a case in which the instruction for starting the tracking has not been received by processor 101 in Step S408 (No in Step S408), the processing loops to Step S404.

In Step S410 (Yes in Step S408), processor 101 performs processing of detecting the athlete on the video image. The detection of the athlete is performed by identifying coordinates (=athlete position) of the athlete in the video image.

In the embodiment, processor 101 detects, as the athlete position, center coordinates of a region in which a differential (=background differential) between a background image (obtained by imaging the swimming pool with no persons in advance) and the image that is being currently displayed is large. Note that the use of the background differential to detect the athlete is not essential, and center coordinates of a region in which an inter-frame differential (a differential between a previous image and a following image) is large may be detected as the athlete position. In addition, pixels in a foreground may be extracted by using color phase components in the image that is being displayed, and center coordinates of a region (foreground region) that is a large region formed by connected pixels of the foreground may be detected as the athlete position.

In the embodiment, the region in which the detection of the athlete is performed is limited in order to enhance accuracy of the detection. This region is referred to as a detection target region. In the embodiment, the detection target region is a region that occupies the surroundings of the athlete position in the previous image. Preferably, it is desirable that the shape of the detection target region be a shape that is biased toward the advancing direction from the athlete position in the previous image. The detection of the athlete is performed for each lane in the embodiment. Therefore, the detection target region is set for each lane. An initial value of the detection target region is a location of 5 to 10 m from the start point (of the real swimming pool). This is because it is often difficult to detect the athlete in the region immediately after the start since the athlete is swimming in a deep part (diving).

The athlete is not necessarily detected even if the processing of detecting the athlete is performed on the video image. For example, it is not possible to detect the athlete in a case in which it is not possible to appropriately extract the background differential, the inter-frame differential, or the foreground region, for example. In the case in which the athlete is swimming in a deep part as described above, it is often not possible to appropriately extract the background differential, the inter-frame differential, the foreground region, or the like. Thus, it is preferable to perform detection result invalidation processing and athlete position correction processing, which will be described later, as needed.

In Step S412, processor 101 overlays and displays the detection result on the athlete position in the video image.

Figure 6:
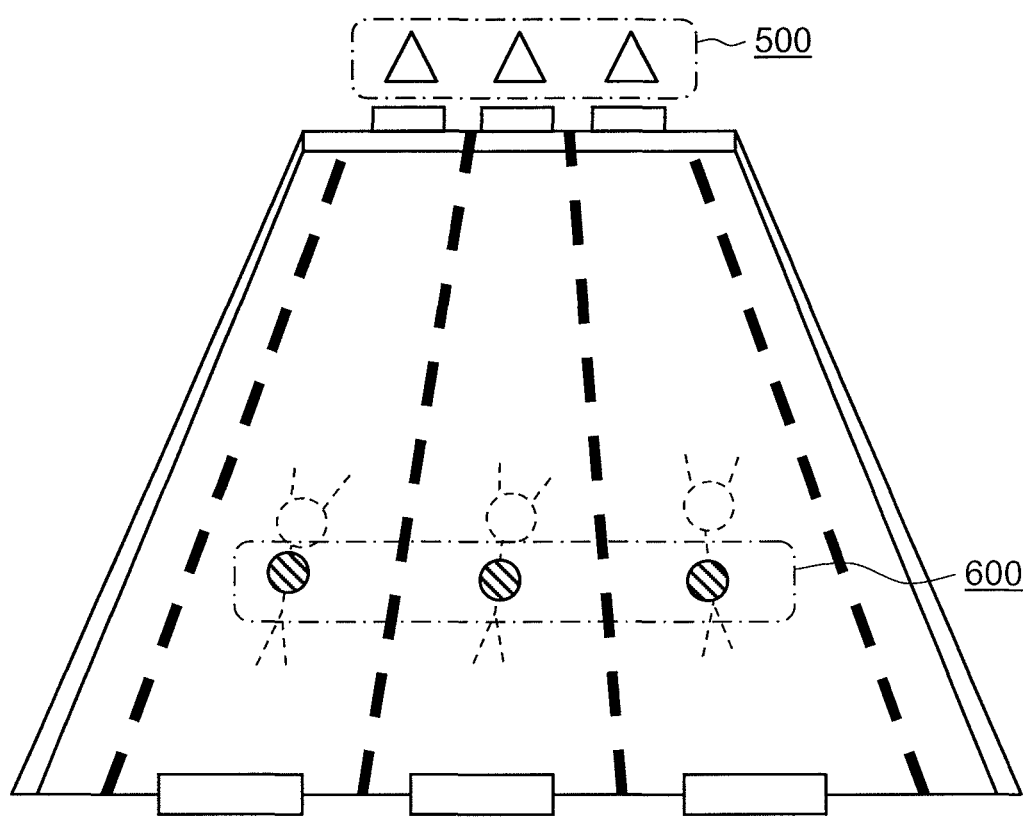
FIG. 6 is a diagram illustrating an example in which a detection result has been overlaid on the video image according to the first exemplary embodiment.

FIG. 6 is a diagram illustrating an example in which the detection result is overlaid on the video image according to the first exemplary embodiment. Detection result 600 is displayed such that it substantially coincides with the athlete position in each lane as illustrated in FIG. 6. Detection result 600 is a circle centered at the athlete position in the embodiment. Note that detection result 600 may not be displayed on the basis of the athlete position itself obtained in Step S410. That is, the display may be performed on the basis of the athlete position corrected on the basis of a history or the like of the previous athlete position or the like. Alternatively, the detection result based on the athlete position itself obtained in Step S410 and the detection result based on the corrected athlete position may be simultaneously displayed for convenience of edition of the video image.

In Step S414, processor 101 updates the detection target region.

In Step S416, processor 101 determines whether or not an instruction for ending the processing has been received from the user of device for identifying a state of an athlete 100. The user of device for identifying a state of an athlete 100 inputs the instruction for ending the processing via input unit 104 after confirming that the competition in the video image has ended. If the instruction for ending the processing is received (Yes in Step S416), the processing performed by the device for identifying a state of an athlete ends.

When the input for the instruction for ending the processing has not been received (No in Step S416), the processing loops to S410. A state in which processing is present in the loop from Step S410 to Step S416 is referred to as an athlete detection processing state.

Hereinafter, processing performed by device for identifying a state of an athlete 100 on the basis of an instruction from the user of device for identifying a state of an athlete 100 in the athlete detection processing state will be described. Note that the following processing is not necessarily performed in parallel when the athlete detection is actually operated. It is also possible to perform the following processing while processor 101 refers to a list of results (a list of athlete positions) obtained after the end of the detection of the athlete in a series of video images.

[1-2-2. Athlete Position Correction Processing]

Figure 7:
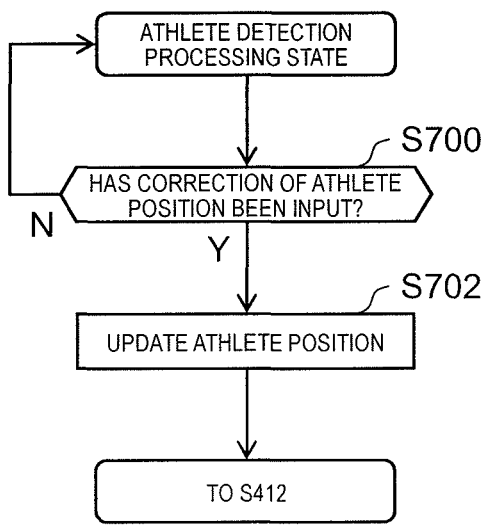
FIG. 7 is a flowchart for describing athlete position correction processing.

FIG. 7 is a flowchart for describing the athlete position correction processing.

In Step S700, processor 101 determines whether or not an instruction for correcting the athlete position has been received from the user of device for identifying a state of an athlete 100.

In a case in which the result of detecting the athlete in Step S410 is incorrect, the user of device for identifying a state of an athlete 100 clicks a location at which the athlete is truly present in the video image. Processor 101 receives the click as the instruction for correcting the athlete position. The input made here is not limited to the clicking operation, and the input may be made through a touch panel or a keyboard as long as it is possible to specify coordinates in the video image.

In Step S702 (Yes in Step S700), processor 101 updates the athlete position obtained in Step S410 with the coordinates clicked in the video image, which have been received as the instruction for correcting the athlete position. If the athlete position is updated, the processing returns to Step S412.

[1-2-3. Detection Result Validating Processing]

Figure 8:
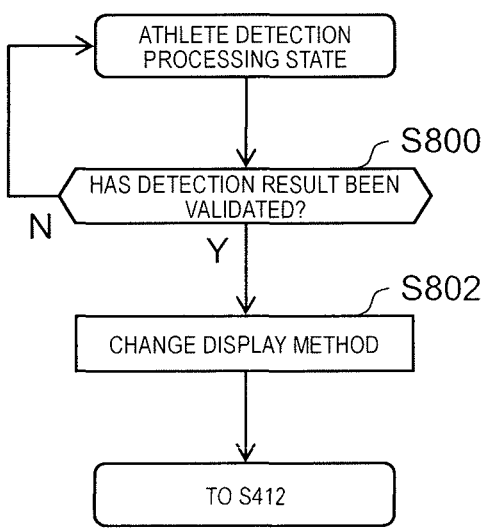
FIG. 8 is a flowchart for describing detection result validating processing.

FIG. 8 is a flowchart for describing the detection result validating processing.

In Step S800, processor 101 determines whether or not an instruction for validating the detection result has been received from the user of device for identifying a state of an athlete 100.

A video image that the user of device for identifying a state of an athlete 100 checks when the user is editing the video image by using device for identifying a state of an athlete 100 is different from a video image of video image content finally obtained by the editing. In the video image of the video image content, CG or the like that represents information (information related to the athlete) representing attributes of the athlete such as a name, a nationality, a swimming speed, and the like of the athlete is overlaid near the athlete in the video image. Meanwhile, there is a case in which the advancing direction and the detection result, which have been described above, are not displayed in the video image content since they are displayed for the user to check the content of the processing performed by device for identifying a state of an athlete 100.

In order to create the video image content, the user obtains information (a state of the athlete) such as the athlete position, the advancing direction, and a speed based on the position by using device for identifying a state of an athlete 100. It is possible to synthesize CG with the video image on the basis of the state of the athlete by passing the state of the athlete to a CG synthesis program. The video image content is generated by synthesizing the CG with the video image. According to the CG synthesis program, for example, video image content in which CG follows the athlete is created by synthesizing the CG in a region that is present in the direction opposite to the advancing direction with reference to the athlete position.

The detection result validating processing is processing of setting the detection result of device for identifying a state of an athlete 100 as being valid. Information about whether the detection result is valid or invalid is a type of information that is to be passed to the CG synthesis program. A CG synthesis program switches a CG display state by performing processing of (1) deciding whether or not to synthesize the CG with the image that has the detection result, (2) changing a state (a color, a shape, letters, and the like) of the CG, or the like, on the basis of whether the detection result is valid/invalid.

In the embodiment, whether the detection result is valid/invalid is switched autonomously by device for identifying a state of an athlete 100 in some cases while the switching is performed on the basis of an instruction from the user in other cases.

In the embodiment, the user can provide an instruction about whether or not the detection result is valid/invalid at any time via input unit 104 in the athlete detection processing state.

In Step S802 (Yes in Step S800), processor 101 changes a method of displaying the detection result on display unit 105. Changing of a color or the like of detection result 600, for example, is exemplified as the changing of the method of displaying the detection result. In this manner, whether or not the detection result is currently valid becomes obvious for the user of device for identifying a state of an athlete 100, and it becomes easy for the user to expect how the video image content is finally completed.

In the embodiment, there is a concern that the athlete position is erroneously detected as if the athlete is present at a further location of 5 m from the starting block when the athlete is present at the starting block, due to the laws of perspective. Thus, processor 101 regards the detection result as being invalid in default setting in the embodiment. Then, it is assumed that the user inputs an instruction for validating the detection result after the user confirms that swimming competition has started and the athlete has swimming about 5 m, in the embodiment.

Note that processor 101 can also automatically perform the detection result validating processing. As a method of automating the detection result validating processing, switching of the detection result as being valid by processor 101 is considered in response to an event in which the background differential is present (1) within about 5 m (a region is set in advance in the video image) from an end of the swimming pool on the side of the start point, (2) with a size that is equal to or greater than a predetermined size (for removing noise), and (3) with a size that is equal to or less than a second predetermined size (for distinction from the athlete on the start point). Note that meeting of the above conditions (1), (2), and (3) in a plurality of images may be added as a condition in order to reduce erroneous detection based on noise in the video image.

If the detection result is switched as being valid, the processing returns to Step S412.

[1-2-4. Detection Result Invalidating Processing]

Figure 9:
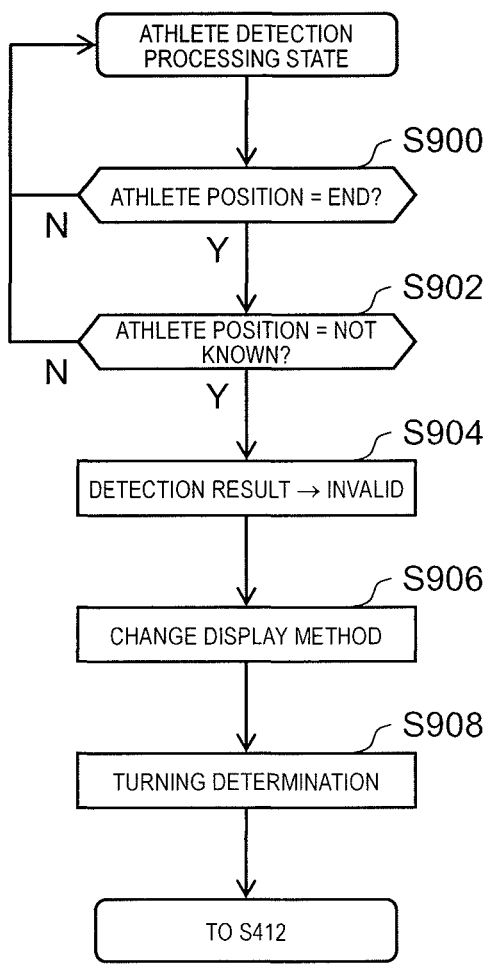
FIG. 9 is a flowchart for describing detection result invalidating processing.

FIG. 9 is a flowchart for describing the detection result invalidating processing.

As described above, there is a concern that the aforementioned athlete detection in Step S410 may be erroneously performed in the case in which the athlete swims in the deep part. Here, the athlete swims in the deep part at ends of the swimming pool (an upper end and a lower end of the swimming pool in FIG. 2 and the like) for turning directions in swimming competition. In addition, since touch panels are installed at the ends of the swimming pool, and it is possible to acquire timings at which the athlete reaches the ends of the lane or the like from data of the touch panel, a demand for acquiring the position from the video image is low.

Therefore, processor 101 performs processing illustrated in FIG. 9 such that the detection result is invalidated, in a case in which the athlete is present at the ends of the swimming pool in the embodiment.

Figure 10:
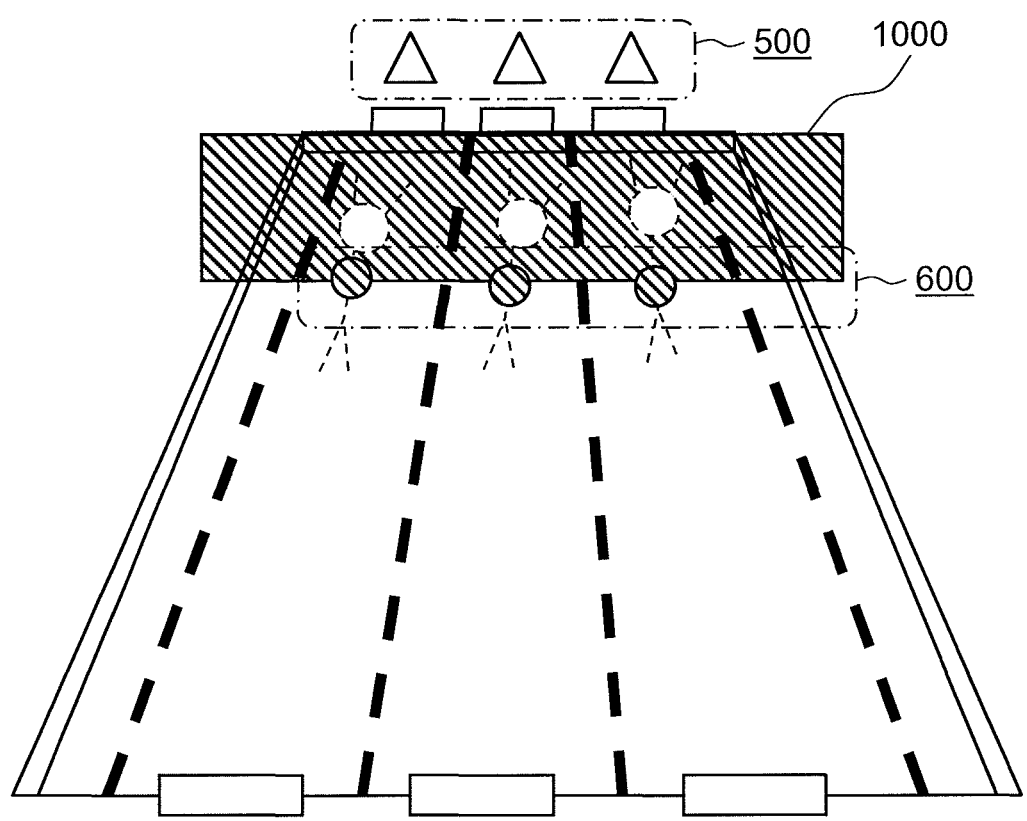
FIG. 10 is a diagram illustrating an example in which an athlete position has approached an end of the swimming pool.

In Step S900, processor 101 determines whether or not the athlete position is present at the ends of the swimming pool. FIG. 10 is a diagram illustrating an example in which the athlete position has approached an end of the swimming pool. As illustrated in FIG. 10, region 1000 at the end of the swimming pool is designated in the video image in advance by the user through input unit 104. If the center of detection result 600 (≈athlete position) is present in region 1000 at the end of the swimming pool as illustrated in FIG. 10, processor 101 determines that the athlete position is present at the end of the swimming pool.

In Step S902 (Yes in Step S900), processor 101 determines whether or not the athlete position is not known. The case in which the athlete position is not known means a case in which the athlete position has not been detected or a case in which the athlete position is within a predetermined range from the previous athlete position. Note that since it is possible to confirm that the athlete position is continuously present at the end again by performing the processing in this step S902, it is possible to amend the result of Step S900 in this step even in a case in which water splash, a judge, or the like is erroneously detected as the athlete. This results in an advantage that reliability of the result of the determination in Step S900 increases by performing this step S902. However, the processing in this step is not essential step for invalidating the detection result.

In Step S904 (Yes in Step S902), processor 101 switches the detection result as being invalid. In the embodiment, it is assumed that the athlete enters the end of the swimming pool after the detection result as being valid is switched to the detection result as being invalid after the start, as described above.

In Step S906, processor 101 changes the method of displaying the detection result on display unit 105. In order to change the method of displaying the detection result, changing a color or the like of detection result 600, for example, is exemplified. In this manner, whether or not the detection result is currently valid becomes obvious for the user of device for identifying a state of an athlete 100, and it becomes easy for the user to expect how the video image content is finally completed.

In Step S908, processor 101 brings an internal state of the processing into a turning determination state. The turning determination state is a state in which turning detection processing as will be described later is performed. Note that the turning detection state is also the athlete detection processing state.

If the detection result is switched as being invalid, the processing returns to Step S412.

[1-2-4-1. Turning Detection Processing]

Figure 11:
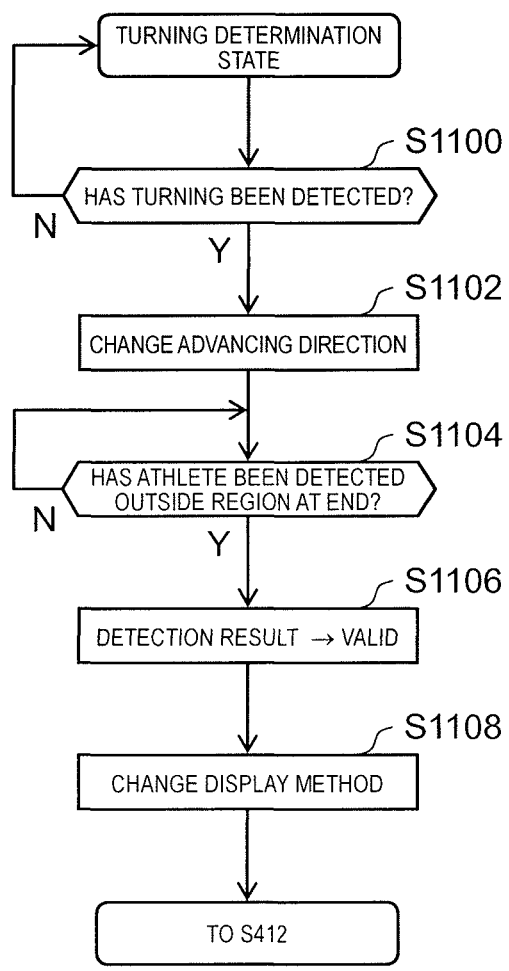
FIG. 11 is a flowchart for describing turning detection processing.

FIG. 11 is a flowchart for describing the turning detection processing.

In Step S908, processing when the turning determination state has been reached will be described. Note that since the turning detection state is also the athlete detection processing state, the loop processing in Step S410 to Step S416 and other processing are also performed in parallel with the turning detection processing even in the turning determination state.

In Step S1100, processor 101 determines whether or not turning has been detected. Processor 101 detects the turning on the basis of the result of the athlete detection. A plurality of methods for detecting the turning on the basis of the result of the athlete detection are considered. In the embodiment, the turning is detected in a case in which the number of times the athlete can be detected in a predetermined period of time (=predetermined frame images) after the athlete detection position is brought into the turning detection state is equal to or less than a threshold value. Since an ordinary period of time required for the turning is known while it is difficult to detect the athlete position during the turning, it is possible to appropriately detect the turning by using such a predetermined reference.

As another method for detecting the turning, provision of a reliability index to the result of the athlete detection is considered, for example. That is, detecting the turning in a case in which the number of times the reliability index is below a predetermined value is equal to or greater than a predetermined number of times, in a predetermined period of time (=predetermined frame images) after the athlete detection position is brought into the turn detection state is considered.

As another method for detecting the turning, regarding the athlete position as being the same as that in the previous frame in a case in which it is not possible to perform the athlete detection is considered, for example. That is, it is considered that the turning is detected in a case in which the number of times the athlete position is within a predetermined range from a location where the turning detection state has previously been achieved is equal to or greater than a predetermined number of times, in a predetermined period of time (=predetermined frame images) after the turning detection state has been achieved.

In Step S1102, processor 101 changes the advancing direction in the lane in which the turning has been detected.

In Step S1104, processor 101 determines whether or not the athlete position has been detected in a region other than region 1000 at the end of the swimming pool. Since there is no demand for synthesizing CG in Step S904 as described above, the detection result is temporarily switched as being invalid. Meanwhile, in a case in which the athlete has exited the region at the end of the swimming pool, the demand for synthesizing the CG is present again. Therefore, processor 101 determines whether or not the athlete position has been detected in a region other than region 1000 at the end of the swimming pool in Step S1104.

In Step S1106 (Yes in Step S1104), processor 101 switches the detection result as being valid.

In Step S1108, processor 101 changes the display method similarly to Step S802.

Figure 12:
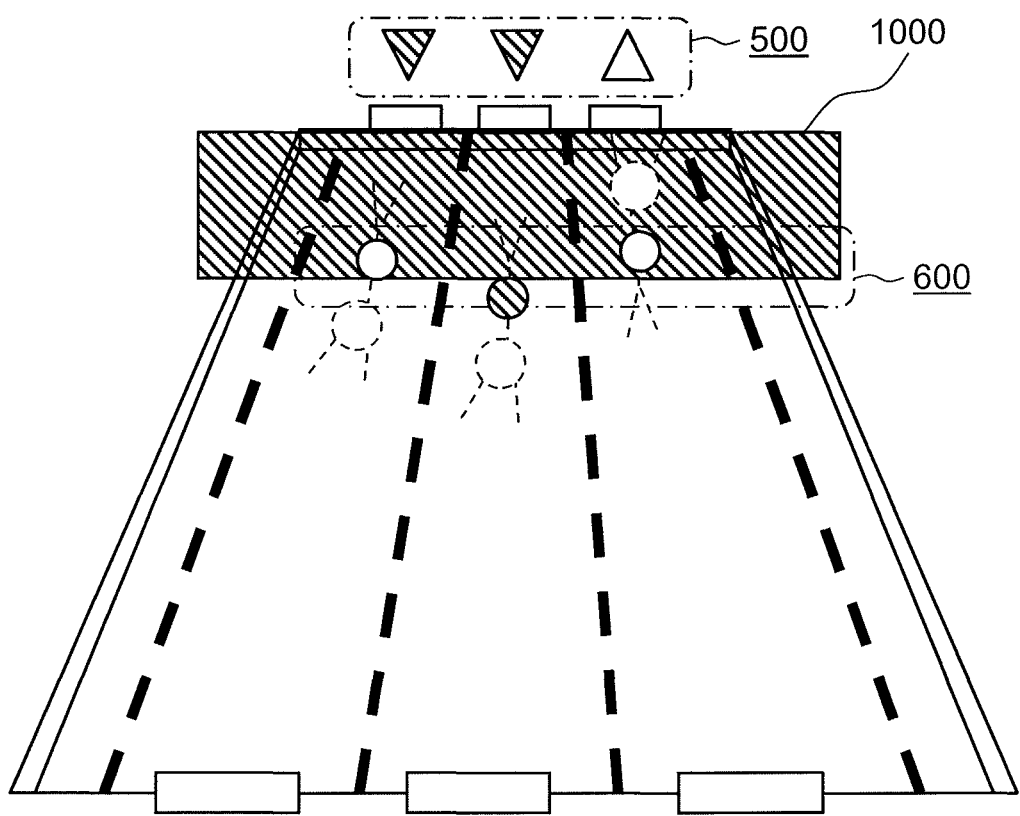
FIG. 12 is a diagram illustrating how a display unit looks when turning is detected according to the first exemplary embodiment.

FIG. 12 is a diagram illustrating how the display unit is like when the turning detection is performed according to the first exemplary embodiment.

As illustrated in FIG. 12, the orientation of advancing direction 500 has been changed to the downward orientation since turning of the athlete at the left end has been detected by processor 101. Note that the color of advancing direction 500 may be changed in accordance with the orientation as illustrated in FIG. 12. In addition, since the detection result for the athlete at the left end has been set as being invalid, the color of detection result 600 is different from those in FIG. 10 and the like.

As illustrated in FIG. 12, since turning of the athlete at the center has been detected by processor 101, and the athlete position has been detected in a region other than region 1000 at the end of the swimming pool, the orientation of advancing direction 500 is a downward orientation, and the color of detection result 600 is the same as that in FIG. 10 and the like.

As illustrated in FIG. 12, since turning of the athlete at the right end has not been detected by processor 101 (yet in the turning determination state), the orientation of advancing direction 500 has not been changed. Since the detection result for the athlete at the left end has been set as being invalid, the color of detection result 600 is different from that in FIG. 10 and the like.

If the turning is detected, and the detection result is switched as being valid, the processing returns to Step S412.

Note that the turning determination state ends. Note that although device for identifying a state of an athlete 100 is adapted to detect the turning and change the advancing direction as described above, processor 101 may perform processing to change the advancing direction on the basis of a user's input in the athlete detection processing state, just in case in which the detection of the turning is failed. This input has an advantage that the user's recognition result can be immediately reflected to the advancing direction if a mouse as input unit 104 is used, and right clicking is performed to identify a lane in the video image, thereby allowing processor 101 to recognize the lane in which the advancing direction is to be changed, for example.

[1-3. Effects and the Like]

As described above, processor 101 in device for identifying a state of an athlete 100 refers to a result of performing processing of detecting an athlete on a video image and identifies an advancing direction of the athlete as a direction that is different from the previous advancing direction on the basis of a result of the detection of the athlete after the athlete is present in a region on the side of the end of the swimming pool according to the embodiment.

In this manner, it is possible to precisely identify a state of the athlete who is present in the swimming pool as described above.

In addition, processor 101 identifies the advancing direction of the athlete as a direction that is different from the previous advancing direction in a case in which the number of times the athlete can be detected in a predetermined period of time after the athlete is present in the region on the side of the end of the swimming pool is equal to or less than a threshold value according to the embodiment.

In this manner, it is possible to more precisely identify a state of the athlete who is present in the swimming pool as described above.

In addition, processor 101 identifies the advancing direction of the athlete as a direction that is different from the previous advancing direction in a case in which the athlete can be detected at a location that is close to a location in the swimming pool, where the state in which the athlete cannot be detected has been achieved, by a predetermined distance or greater after the athlete is present in the region on the side of the end of the swimming pool according to the embodiment. In this manner, it is possible to more precisely identify the region of the lane that is present in the image since precision of calculating a pattern is improved. In this manner, it is possible to more precisely identify the state of the athlete who is present in the swimming pool as described above.

In addition, processor 101 generates display control information for switching a display state of information (whether the detection result is valid/invalid in the embodiment) when information related to the athlete is synthesized with the video image, and in a case in which the athlete is present in the region on the side of the end of the swimming pool, processor 101 sets the display control information as information indicating that information related to the athlete is not to be displayed according to the embodiment. In this manner, it is possible to improve efficiency for creating video image content by using the athlete state.

In addition, processor 101 generates display control information for switching a display state of information for synthesizing the information related to the athlete with the video image, and in a case in which the athlete is detected from the video image outside the region on the side of the end of the swimming pool after the advancing direction of the athlete is identified as the direction that is different from the advancing direction, processor 101 sets the display control information as information indicating that the information related to the athlete is to be displayed. In this manner, it is also possible to improve the efficiency for creating video image content by using the athlete state.

As described above, the embodiment has been described as an example of the technologies of the present disclosure. For this reason, the accompanying drawings and the detailed description have been provided.

Therefore, the components illustrated in the accompanying drawings and the detailed description can include not only components essential for solving the problems but also components that are not essential for solving the problems in order to describe the above technologies as an example. Therefore, the components that are not essential should not be immediately recognized as being essential on the basis of the illustration of the components, which are not essential, in the accompanying drawings and the detailed description.

Also, since the aforementioned embodiment is for describing the technologies of the present disclosure as an example, various modifications, replacements, additions, omissions, and the like may be made within the scope of the claims or a scope equivalent thereto.

Similarly, the technologies of the present disclosure are not limited thereto and can also be applied to embodiments achieved by modifications, replacements, additions, omissions, and the like being made. In addition, new embodiments can also be achieved by combining the respective components described in the aforementioned first exemplary embodiment.

Thus, other embodiments will be described as examples below.

In the first exemplary embodiment, the processing of detecting the athlete is performed on the video image in Step S410. In another embodiment, precision of the detection may be enhanced by adding the following processing to the processing in Step S410.

That is, processing of invalidating the detection result in a case in which coordinates of the detection invalid region are defined for each lane in advance by recording the coordinates in storage unit 102 and the athlete is detected in the detection invalid region may be added to S410. In a case in which the detection result is invalidated, it is preferable that the athlete position is defined on the basis of a history of positions at which the athlete has previously been detected. As one example of the processing of defining the athlete position on the basis of the history of the positions at which the athlete has been detected, defining of the athlete position on the assumption that the athlete is performing linear motion at an equal speed is exemplified.

The aforementioned processing is effective in a case in which there is a region where the athlete tends to be erroneously detected. The region in which the athlete tends to be erroneously detected can occur due to properties of the camera, properties of the lane, and properties of the arena. Since it is possible to define, as the athlete position, a position at which the athlete is likely present after invalidating the erroneous detection and to thereby improve precision of the athlete detection.

Although region 1000 at the end of the swimming pool is a fixed region according to the first exemplary embodiment, this may be replaced with a region with a size changing in accordance with the advancing direction of the athlete.

That is, in a case in which the end of the swimming pool is present in front of the advancing direction of the athlete, region 1000 at the end of the swimming pool may be defined as being shorter (narrower toward the end of the swimming pool) as compared with a case in which the end of the swimming pool is present behind the advancing direction of the athlete. Specifically, since region 1000 at the end of the swimming pool is designated by the user, it is only necessary for processor 101 to calculate the perspective direction of the region so as to satisfy the aforementioned condition with reference to the size of the designated region.

The aforementioned processing is effective since it is possible to extend the period of time during which the athlete detection result is valid. One of meanings of defining region 1000 at the end of the swimming pool is for avoiding erroneous detection in a case in which the athlete is diving. However, a section in which the athlete dives is shorter in a case in which the end of the swimming pool is present in the advancing direction of the athlete than a section in which the athlete dives in a case in which the end of the swimming pool is present on the side opposite to the advancing direction of the athlete. This is because the athlete performs diving (after the athlete turns) in a case in which the end of the swimming pool is present on the side opposite to the advancing direction of the athlete, while such an event does not occur in a case in which the end of the swimming pool is present in the advancing direction of the athlete. Therefore, it is possible to extend the period of time during which the athlete detection result is valid by changing the size of region 1000 at the end of the swimming pool in accordance with the advancing direction of the athlete as described above. If it is possible to extend the period of time during which the athlete detection result is valid, it is also possible to extend a period of time during which CG can be synthesized.

Also, processing of calculating an order of athletes may be added to the processing described in the first exemplary embodiment.

As an example of a method of calculating the order of athletes, a method of calculating the order from athlete positions and number of times the athletes have turned is exemplified. If only the athlete positions are used, a case in which a certain athlete is present at the same position before and after turning is considered. Thus, it is possible to accurately calculate the order by taking the number of times the athlete has turned into consideration.

Here, in a case in which the order of the athletes is displayed with CG or the like, persons who view the CG or the like may not like rapid changes in the order of the athletes. In such a case, it is preferable to calculate the order of the athletes from a history of orders in the past, and for example, orders in a past several seconds are added, and an athlete with the smallest total value is displayed as a first order, an athlete with the second smallest total value is displayed as a second order.

Note that there is a case in which calculated orders of athletes are the same. In a case in which it is not desirable to calculate such a result that a plurality of athletes are present in the same order, the calculated order may be corrected in accordance with the following priority. As examples of the priority, it is considered (1) that an athlete with a relatively large amount (speed) of movement per unit time is regarded as an athlete in a higher order, (2) that an athlete who is present at the center lane is regarded as an athlete in a higher order, and the like. It is preferable that the order be corrected in accordance with the priority in (1) first, and then if there are athletes in the same order, the order be corrected in accordance with the priority in (2). Since even if there are athletes who are instantaneously present at similarly positions, a variation in the order immediately after that is expected, there is no big problem if the order is corrected according to the reference in (1). Since ability of the athlete who is present at the center lane is typically considered to be high in swimming competition, there is no big problem if the order is corrected according to the reference in (2).

Although the processing is performed on an arena (swimming pool) with a shape that appears in the video image in the first exemplary embodiment, the processing in the first exemplary embodiment may be performed by adding processing of correcting the shape of the arena.

That is, the user may designate four upper-lower left-right corners of the arena that appears in the video image, and processor 101 may convert the shape of the arena into any rectangle (for example, a square with a sufficient size) by performing trapezoidal correction on a coordinate system in the video image on the basis of the coordinates of the four corners.

In this manner, it is possible to further improve precision of the athlete detection. For example, there is a case in which the further side of the lane becomes excessively small due to perspective depending on an angle of a camera installed in the arena, and the precision of the processing in the first exemplary embodiment may deteriorate. In a case in which the imaged arena laterally faces, it is necessary to convert the arena into an arena that longitudinally faces in order to directly (without changing the content of the program) perform the processing in the first exemplary embodiment. Since the shape of the imaged arena is normalized by performing the aforementioned processing of trapezoidal correction on the coordinate system in the video image, it is possible to stably perform the processing in the first exemplary embodiment. In a case in which the aforementioned processing of performing trapezoidal correction on the coordinate system in the video image is performed, an arena video image after the trapezoidal correction may be displayed along with the captured video image with no change, and the aforementioned athlete position correction processing may be performed on the arena video image after the trapezoidal correction. Since the lane positioned at a further location from the camera appears to be small in the captured video image with no change in the case in which the imaged arena laterally faces, it is difficult to check and click a location at which the athlete is truly present in the video image in the athlete position correction processing. Since the shape of the imaged arena is normalized on the aforementioned arena video image after the trapezoidal correction, it is possible to precisely check and click the location at which the athlete is truly present.

INDUSTRIAL APPLICABILITY

The present disclosure can be applied to a method or a device for identifying a state of an athlete in a video image. For example, it is possible to apply the present disclosure to a computer for handling analysis of a video image or the like of a sport, for example.

Reference Marks in the Drawings

100 DEVICE FOR IDENTIFYING STATE OF ATHLETE

101 PROCESSOR
102 STORAGE UNIT
103 COMMUNICATION UNIT
104 INPUT UNIT
105 DISPLAY UNIT
106 BUS
200 IMAGING DEVICE
300 SWIMMING POOL
302 LANE MARK
310 ATHLETE
500 ADVANCING DIRECTION
600 DETECTION RESULT
1000 REGION

The invention claimed is:

1. A method for identifying, the method comprising:
referring, by a processor, to a result of performing processing of detecting an athlete that is present in a video image, the video image being captured from outside water of a swimming pool;
identifying, by the processor, an advancing direction of the athlete as a direction that is different from a previous advancing direction, in a case where a number of times the athlete is detected from the video image in a time period expected to be required for turning after the athlete is present in a region on a side of an end of the swimming pool is equal to or less than a threshold value; and
maintaining the advancing direction of the athlete as the previous advancing direction in a case where turning is not detected,
wherein the turning is detected in the case where the number of times the athlete is detected from the video image in the time period expected to be required for turning after the athlete is present in the region on the side of the end of the swimming pool is equal to or less than the threshold value.

2. The method of claim 1, further comprising:
generating, by the processor, display control information for switching a display state of information related to the athlete when the information related to the athlete is synthesized with the video image; and
setting, by the processor, the display control information as information indicating that the information related to the athlete is not to be displayed in a case in which the athlete is present in the region on the side of the end of the swimming pool.

3. The method of claim 1, further comprising:
generating, by the processor, display control information for switching a display state of information related to the athlete when the information related to the athlete is synthesized with the video image; and
setting, by the processor, the display control information as information indicating that the information related to the athlete is to be displayed in a case in which the athlete is detected outside the region on the side of the end of the swimming pool in the video image after the advancing direction of the athlete is identified as the direction that is different from the previous advancing direction.

4. The method of claim 1, further comprising:
determining, by the processor, that turning of the athlete does not occur when the case, in which the number of times the athlete is detected from the video image in the time period expected to be required for turning after the athlete is present in the region on the side of the end of the swimming pool is equal to or less than the threshold value, is not detected.

5. The method of claim 1, further comprising:
repeating, by the processor, a turning determination state in which the processor determines whether the turning is detected in response to the advancing direction of the athlete being maintained as the previous advancing direction.

6. The method of claim 5, wherein the advancing direction of the athlete is maintained as the previous advancing direction by not changing the previous advancing direction.

7. A device for identifying, the device comprising:
a processor; and
a memory including a program that, when executed by the processor, causes the processor to perform operations, the operations including:
referring to a result of performing processing of detecting an athlete that is present in a video image, the video image being captured from outside water of a swimming pool;
identifying an advancing direction of the athlete as a direction that is different from a previous advancing direction, in a case where a number of times the athlete is detected from the video image in a time period expected to be required for turning after the athlete is present in a region on a side of an end of the swimming pool is equal to or less than a threshold value; and
maintaining the advancing direction of the athlete as the previous advancing direction in a case where turning is not detected,
wherein the turning is detected in the case where the number of times the athlete is detected from the video image in the time period expected to be required for turning after the athlete is present in the region on the side of the end of the swimming pool is equal to or less than the threshold value.

8. The device of claim 7, wherein the operations further include:
generating display control information for switching a display state of information related to the athlete when the information is synthesized with the video image; and
setting the display control information as information indicating that the information related to the athlete is not to be displayed in a case in which the athlete is present in the region on the side of the end of the swimming pool.

9. The device of claim 7, wherein the operations further include:
generating display control information for switching a display state of information related to the athlete when the information is synthesized with the video image; and
setting the display control information as information indicating that the information related to the athlete is to be displayed in a case in which the athlete is detected outside the region on the side of the end of the swimming pool in the video image after the advancing direction of the athlete is identified as the direction that is different from the previous advancing direction.

10. The device of claim 7, wherein the operations further include:
determining that turning of the athlete does not occur when the case, in which the number of times the athlete is detected from the video image in the time period expected to be required for turning after the athlete is present in the region on the side of the end of the swimming pool is equal to or less than the threshold value, is not detected.

11. The device of claim 7, wherein the operations further include:
repeating a turning determination state in which the processor determines whether the turning is detected in response to the advancing direction of the athlete being maintained as the previous advancing direction.

12. The device of claim 11, wherein the advancing direction of the athlete is maintained as the previous advancing direction by not changing the previous advancing direction.

13. A method for identifying, the method comprising:
referring, by a processor, to a result of performing processing of detecting an athlete that is present in a video image, the video image being captured from outside water of a swimming pool;
identifying, by the processor, an advancing direction of the athlete as a direction that is different from a previous advancing direction, in a case where a number of times the athlete is detected from the video image in a time period expected to be required for turning after the athlete is present in a region on a side of an end of the swimming pool is equal to or less than a threshold value; and
identifying, by the processor, the advancing direction of the athlete as the previous advancing direction, which is not changed, in a case where the number of times the athlete is detected from the video image in the time period expected to be required for turning after the athlete is present in the region on the side of the end of the swimming pool is more than the threshold value.

14. A device for identifying, the device comprising:
a processor; and
a memory including a program that, when executed by the processor, causes the processor to perform operations, the operations including:
referring to a result of performing processing of detecting an athlete that is present in a video image, the video image being captured from outside water of a swimming pool;
identifying an advancing direction of the athlete as a direction that is different from a previous advancing direction, in a case where a number of times the athlete is detected from the video image in a time period expected to be required for turning after the athlete is present in a region on a side of an end of the swimming pool is equal to or less than a threshold value; and
identifying the advancing direction of the athlete as the previous advancing direction, which is not changed, in a case where the number of times the athlete is detected from the video image in the time period expected to be required for turning after the athlete is present in the region on the side of the end of the swimming pool is more than the threshold value.

* * * * *